United States Patent
Shirley et al.

[11] Patent Number: 5,951,550
[45] Date of Patent: Sep. 14, 1999

[54] ENDOCERVICAL CONIZATION ELECTRODE APPARATUS

[75] Inventors: Ben Shirley, Salt Lake City, Utah; Walter Prendiville, Dublin, Ireland

[73] Assignee: Utah Medical Products, Inc., Midvale, Utah

[21] Appl. No.: 09/038,658

[22] Filed: Mar. 11, 1998

[51] Int. Cl.[6] .................................................. A61B 17/39
[52] U.S. Cl. ............................................. 606/45; 600/564
[58] Field of Search ................................. 606/41, 45, 47, 606/49; 600/564

[56] References Cited

U.S. PATENT DOCUMENTS

| | | | |
|---|---|---|---|
| 2,447,169 | 8/1948 | Sousa | 606/45 |
| 3,943,916 | 3/1976 | Vadas | 128/2 |
| 4,493,320 | 1/1985 | Treat | 128/303.15 |
| 5,032,124 | 7/1991 | Menton | 606/19 |
| 5,047,042 | 9/1991 | Jerath | 606/167 |
| 5,403,310 | 4/1995 | Fischer | 606/45 |
| 5,554,159 | 9/1996 | Fischer | 606/45 |
| 5,626,577 | 5/1997 | Harris | 606/45 |
| 5,860,976 | 1/1999 | Billings et al. | 606/41 |

OTHER PUBLICATIONS

Advertisement and product information for Fischer Cone Biopsy Excisor manufactured by Apple Medical Corporation, 580 Main Street, Bolton, MA 01740.

*Primary Examiner*—Lee Cohen
*Attorney, Agent, or Firm*—Madson & Metcalf

[57] ABSTRACT

An electrosurgical cutting device for excising a tissue specimen from a uterine cervix having a substantially constant section. The electrosurgical cutting device including a conducting member operably disposed in relation to a non-conductive support assembly. The support assembly is formed comprising an operative tip having a size sufficient for insertion into a uterine cervical canal and an extension member disposed substantially outward from the axis of an intermediate body portion of the support assembly. Extending arcuately away in a radial direction from a point of substantial tangency to the intermediate body portion of the support assembly, the extension member includes a surface facing facilitating a structural stop for limiting the insertion depth of the operative tip through the cervical canal. The conducting member is formed of a material suitable for conducting high frequency electrical energy for cutting body tissue. Accordingly, the conducting member is in electrical communication with an electrosurgical generator suitable for transmitting sufficient high frequency electrical energy to the conducting member, thereby enabling the conducting member to excise a tissue specimen from the cervical canal. The conducting member is disposed between a distal end of the extension member and a portion of the intermediate body portion of the support assembly. Preferably, the conducting member is a wire electrode having an anatomically-favorable shape adapted to limit excess removal of healthy tissue at a midsection of an excision site. Specifically, the conducting member is effective to be anatomically conformable to the cervical canal so as to provide a tissue specimen having a substantially constant section upon circumferential rotation of the support assembly.

20 Claims, 5 Drawing Sheets

ENDOCERVICAL CONIZATION ELECTRODE APPARATUS

BACKGROUND OF THE INVENTION

1. Field of the Invention

This invention relates to medical instrumentation for surgically cutting body tissue, and more specifically, to novel electrosurgical cutting apparatus for excising a tissue specimen from a female uterine cervix by means of endocervical conization.

2. Technical Background

Cervical Intraepithelial Neoplasia (CIN), a virally-induced disease commonly found in sexually active women, has been shown to be a precursor to cervical cancer. CIN frequently occurs and often coexists in the cervix, vagina and vulva of the female reproductive system. Early diagnosis and management of CIN, therefore, is essential in the prevention of disease progression to invasive cancer.

Improvements in cytologic assessment and evaluation has led to the identification of early precursor lesions. Typically, the first clue to the presence of cervical neoplasia (e.g., tumor formations) is an abnormal Pap smear. In such tests, a small amount of tissue is usually scraped from the interior walls of the uterus and the uterine cervix and pathologically examined to determine if abnormal or pre-cancerous cells are present. If abnormal or pre-cancerous cells are found, the significant features for a diagnosis of CIN typically include cellular immaturity, cellular disorganization, nuclear abnormalities and increased mitotic activity. The extent of the mitotic activity, immature cellular proliferation and nuclear atypicality is generally used to identify the degree of cervical neoplasia.

It is important, however, to acknowledge that the histologic appearance of a lesion does not unequivocally predict whether it represents a simple productive viral infection or a neoplasm. Some low-grade lesions can be classified as productive viral infections, but others contain cancer-associated human papillomavirus (HPV) types and have the biologic features of a precursor lesion. In this regard, endocervical conization procedures have been developed by those skilled in the art for the management of CIN and precursor lesions that may progress to invasive carcinoma.

Traditionally, cervical conization procedures are performed by a surgeon using a conventional scalpel inserted through the vagina to the uterine cervix which may be secured in place by one or more surgical clamps. The scalpel is carefully manipulated in a circular pattern about the mouth of the cervix while attempting to maintain the blade at a constant acute angle relative to the cervical canal in order to cut and remove a symmetrical tissue sample. A serious disadvantage with free-hand surgical cutting techniques and methods of the prior art is that it is virtually impossible to excise an ideal tissue sample which is configured having a symmetrical shape sufficient for accurate and reliable analytical testing by a pathologist. In this regard, a prognosis is highly dependent upon the tissue sample having a constant angle about its circumference and that is symmetric (capable of division by a longitudinal plane into similar halves which correspond in size, shape and relative position on opposite sides of a dividing line or median plane or about a center or axis) about the central canal of the cervix from which it has been excised. Accordingly, the regularity and symmetry of the tissue samples collected by means of prior art free-hand techniques are generally conditional upon the skill and expertise of the surgeon.

Based on the foregoing disadvantages associated with free-hand techniques, those skilled in the art developed surgical instruments for performing endocervical conization comprising at least one cutting blade having a selectively fixed relationship to a handle member. For example, prior art surgical instruments for performing cold-knife conization of the cervix were developed consisting of a two part body having an elongated main portion, a separate distal end secured to the main portion and a pair of round nose, pivotal blades disposed on opposing sides of the main portion adjacent the distal end. In operation, the pivotal blades may be simultaneously rotated and progressively advanced or retracted by means of the combined rotary and linear motion of an actuator and internal cam assembly. These prior art cold-knife surgical instruments are generally manipulated by holding a grip in one hand and rotating a handle with the other hand, which action rotates the entire body and hence the pivotal blades. Upon revolution, the blades advance so as to produce a "helicoid" cutting path in contiguous cervical tissue.

In accordance with other such prior art apparatus and techniques for performing cold-knife conization, those skilled in the art developed surgical instruments having first and second elongated arms pivotally connected together intermediate their ends to provide for scissor-like relative movement. Mounted at one end of the first arm is a coextensive probe sized to be inserted into a female cervical canal. A corresponding end of the second arm secures a surgical cutting blade at an acute cutting angle relative to the probe with the apex of the angle located adjacent the distal end of the probe. The cutting blade can alternatively be moved toward and away from the probe by pivotal manipulation of the arms. In operation, the arms are mutually pivoted to cause the single cutting blade to pierce and slice through cervical tissue. In this manner, the instrument may be rotated gently about the longitudinal axis of the probe to move the cutting blade in a circular pattern about the cervical canal to excise a cone-shaped tissue sample for pathological study and diagnosis.

Despite the development and use of prior art cold-knife conization apparatus and techniques as described above, the overall effectiveness of such prior art devices has been questioned because of the excessive removal of healthy tissue, the uncertainty whether the full extent of the lesion has been removed, post-operative recovery time and the potential for severe bleeding. To overcome several deficiencies of prior art cold-knife devices, electrosurgical instruments were developed that provide a means for cutting and/or cauterizing body tissue while demonstrating fewer risks and complications than those associated with cold-knife conization. In particular, electrosurgical instruments and techniques generally reduce blood loss, operative time and post-operative patient recovery time.

One such prior art electrosurgical device comprises an instrument channel for slidably receiving a cutting surgical electrode disposed in the form of a loop or snare. The surgical snare may be extended or withdrawn from the end of an endoscope and made to surround an undesirable growth within a body organ or cavity by means of an actuator. To resect the growth, the snare is generally positioned around the base of the growth and tightened so as to gather the tissue where the growth adjoins the wall of healthy tissue. A meaningful advantage of electrosurgical procedures of the prior art is that they are relatively bloodless as a result of immediate cauterization of the tissue as the loop or snare electrode cuts through it.

Electrodes for endocervical conization have also been developed which include a thin triangular or linear wire extending in a straight line between a probe and a support member. A significant disadvantage with utilizing prior art electrosurgical devices for endocervical conization which comprise a triangular or linearly disposed cutting wire is that they tend to produce greater thermal injury to the specimen and intact cervical tissue than medically desirable, thus having the potential for leading to reproductive and/or obstetric sequelae. Excessive healthy tissue disposed near the proximal tip(s) of the cutting wire and the middle section of the excision are typically removed unnecessarily, thus leading to poor interpretation by pathologists because of excess thermal injury. Moreover, since CIN lesions generally extend no more than 8 mm into the cervical tissue, the removal of excess tissue results in needless thermal injury to the surrounding healthy tissue and will therefore typically lengthen post-operative recovery time.

While the prior art electrosurgical devices disclosed above may appear generally suitable for their intended purposes, these prior art electrosurgical devices nevertheless leave much to be desired from the standpoint of excessive tissue removal, thermal injury to surrounding healthy tissue and effectiveness of operation. In accordance therewith, it would be desirable as a diagnostic and therapeutic modality to provide an improved electrosurgical cutting apparatus for endocervical conization which realizes the advantages of the wire electrode while at the same time eliminating the disadvantages associated therewith.

Such an electrosurgical cutting device is disclosed and claimed herein.

BRIEF SUMMARY AND OBJECTS OF THE INVENTION

In view of the foregoing, it is a primary object of the present invention to provide novel electrosurgical cutting apparatus for excising a tissue specimen from a female uterine cervix by means of endocervical conization.

It is also an object of the present invention to provide an electrosurgical cutting apparatus providing a diagnostic and therapeutic modality designed to efficiently cut body tissue through the process of cell lysis using heat produced by electrical current which may be concentrated at an endocervical site where cutting is desired.

It is a further object of the present invention to provide an electrosurgical cutting apparatus for performing endocervical conization which comprises a thin, wire electrode connected to a source of high frequency electrical energy. The wire electrode being configured having an anatomically-favorable curve adapted to limit excess removal of healthy tissue at the midsection and opposing ends of an excision site, while providing a tissue specimen having a substantially constant section. The anatomically-favored curve of the electrode of the present invention may be adapted to facilitate a relatively deeper or wider cut in relation to the excision of a tissue specimen from the cervical canal.

It is a still further object of the present invention to provide an electrosurgical cutting apparatus for performing endocervical conization which includes a non-conductive support member comprising an operative tip having a size sufficient for insertion through a uterine cervical canal and an extension member including a surface facing having a general arcuate shape which facilitates a structural stop for limiting insertion of the operative tip into the cervical canal. Structurally, a wire electrode having an anatomically-favorable curve is operably disposed between an upper portion of the extension member and the operative tip, thus providing a means for limiting excess removal of healthy tissue at the midsection at opposing ends of an endocervical excision site.

Additionally, it is an object of the present invention to provide an electrosurgical cutting apparatus for performing endocervical conization with precision and accuracy, while providing a tissue specimen having a substantially constant section thus reducing unnecessary thermal exposure to healthy tissue.

Consistent with the foregoing objects, and in accordance with the invention as embodied and broadly described herein, an endocervical cutting apparatus for excising a tissue specimen having a substantially constant section from a uterine cervix is disclosed in one preferred embodiment of the present invention as including a conducting member disposed in relation to a non-conductive support assembly. The support assembly is preferably formed of a rigid, thermally stable, non-conductive material and includes an internal channel having an insulated core. Structurally, the support assembly may be formed comprising an operative tip having a size sufficient for insertion into a uterine cervical canal and an extension member disposed substantially perpendicular to an axis of an intermediate body portion of the support assembly. Extending arcuately away in a radial direction from a point of substantial tangency in relation to the intermediate body portion of the support assembly, the extension member includes a surface facing having a general concave configuration which facilitates a structural stop for limiting the insertion depth of the operative tip into the cervical canal.

Disposed in operable relation to the support assembly, the conducting member is formed of a material suitable for conducting high frequency electrical energy sufficient for cutting body tissue. Correspondingly, the conducting member is in electrical communication with an electrosurgical generator suitable for transmitting high frequency electrical energy to the conducting member, thereby enabling the conducting member to excise a tissue specimen from the cervical canal. In preferred structural design, the conducting member is disposed between a distal end of the extension member and a portion of the intermediate body portion of the support assembly. The conducting member preferably comprises a wire electrode having an anatomically-favorable shape adapted to limit excess removal of healthy tissue at a midsection and opposing ends of an excision site. Specifically, the conducting member is effective to be anatomically conformable to the cervical canal so as to provide a tissue specimen having a substantially constant section upon the circumferential rotation of the support assembly.

In the course of operation, the electrosurgical generator produces high frequency energy which is transmitted through the connecting wire to the conducting member. The surgeon generally guides the conducting member to the specified area of body tissue where the incision is to occur. With the operative tip inserted within the cervical canal at a depth limitation consistent with the structural stop formed by the surface facing of the extension member, the electrosurgical cutting apparatus of the present invention may be rotated about the longitudinal axis of the intermediate body portion of the support assembly. By manipulating the anatomically-favorable configuration of the conducting member in a circular motion about the cervical canal, a tissue sample having a substantially constant section is excised for pathological study and diagnosis, thereby reducing unnecessary thermal exposure to healthy tissue which could result in reproductive and/or obstetric sequelae.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DESCRIPTION OF THE PREFERRED EMBODIMENT

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 5, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Figure 1:
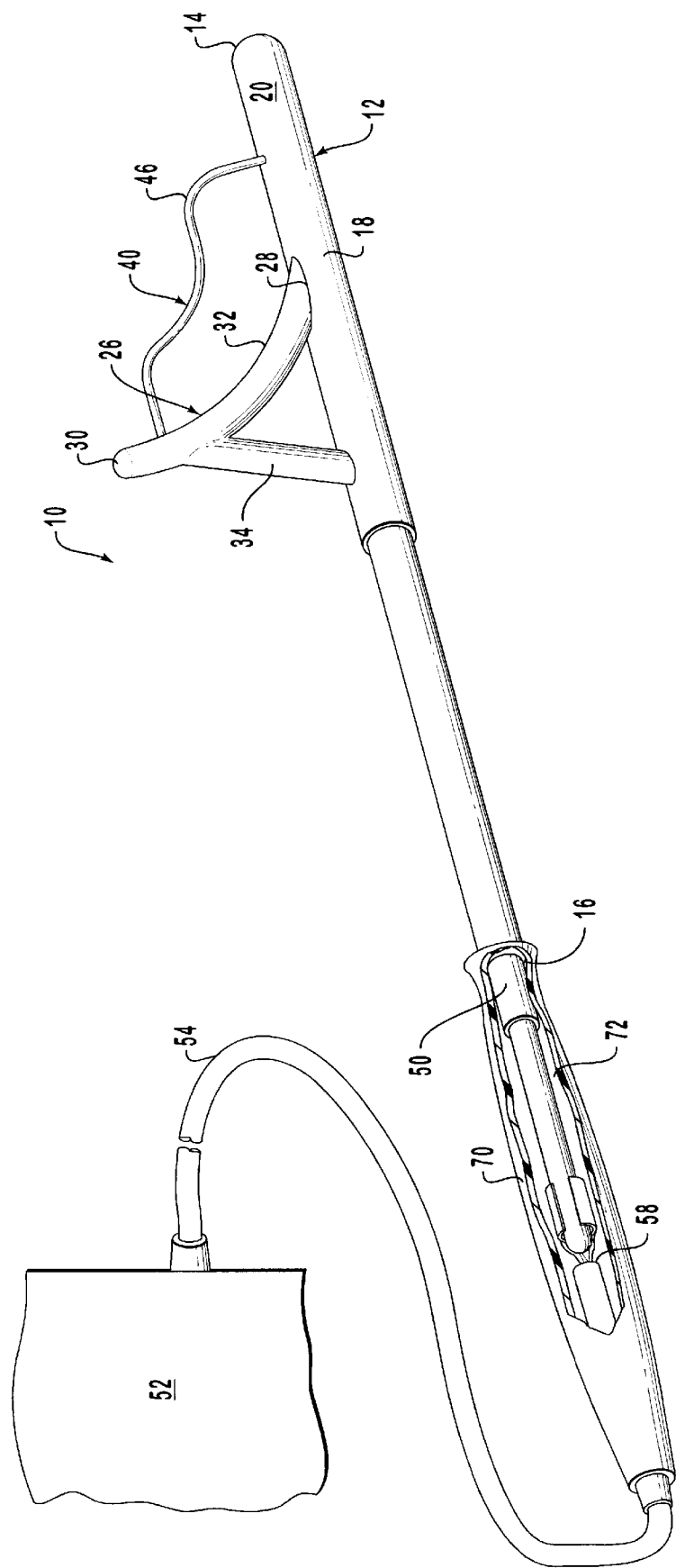
FIG. 1 is a perspective view an endocervical conization electrode apparatus in accordance with one presently preferred embodiment of the present invention.
Figure 2:
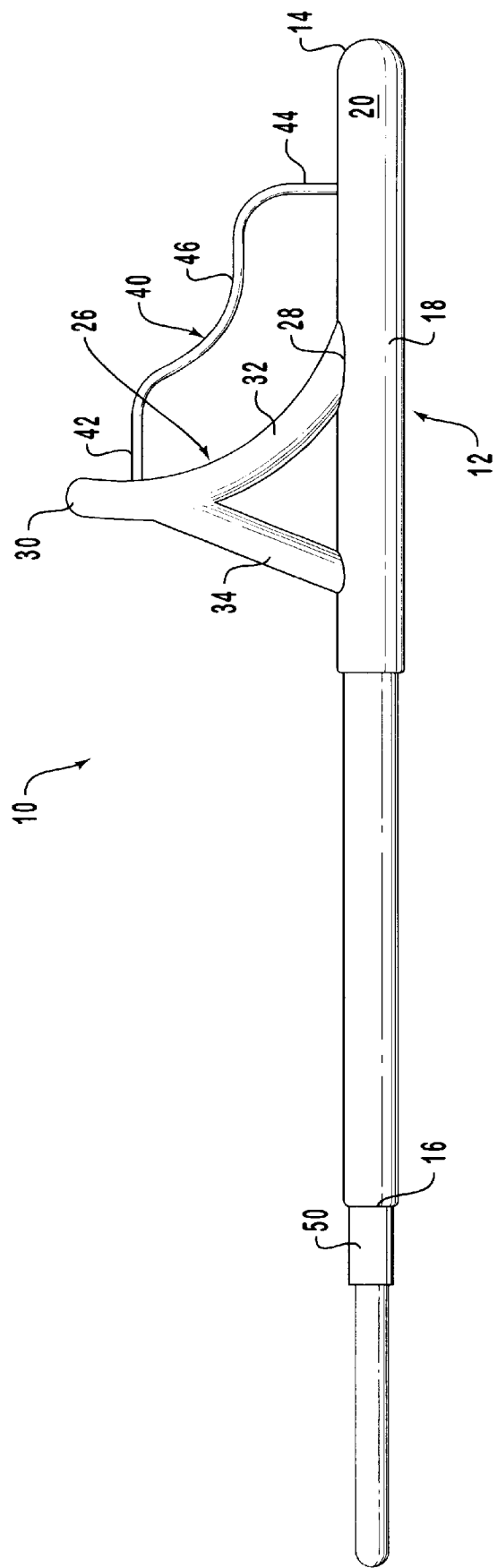
FIG. 2 is an elevational side view of one presently preferred embodiment of the endocervical conization electrode apparatus as illustrated in FIG. 1.
Figure 3:
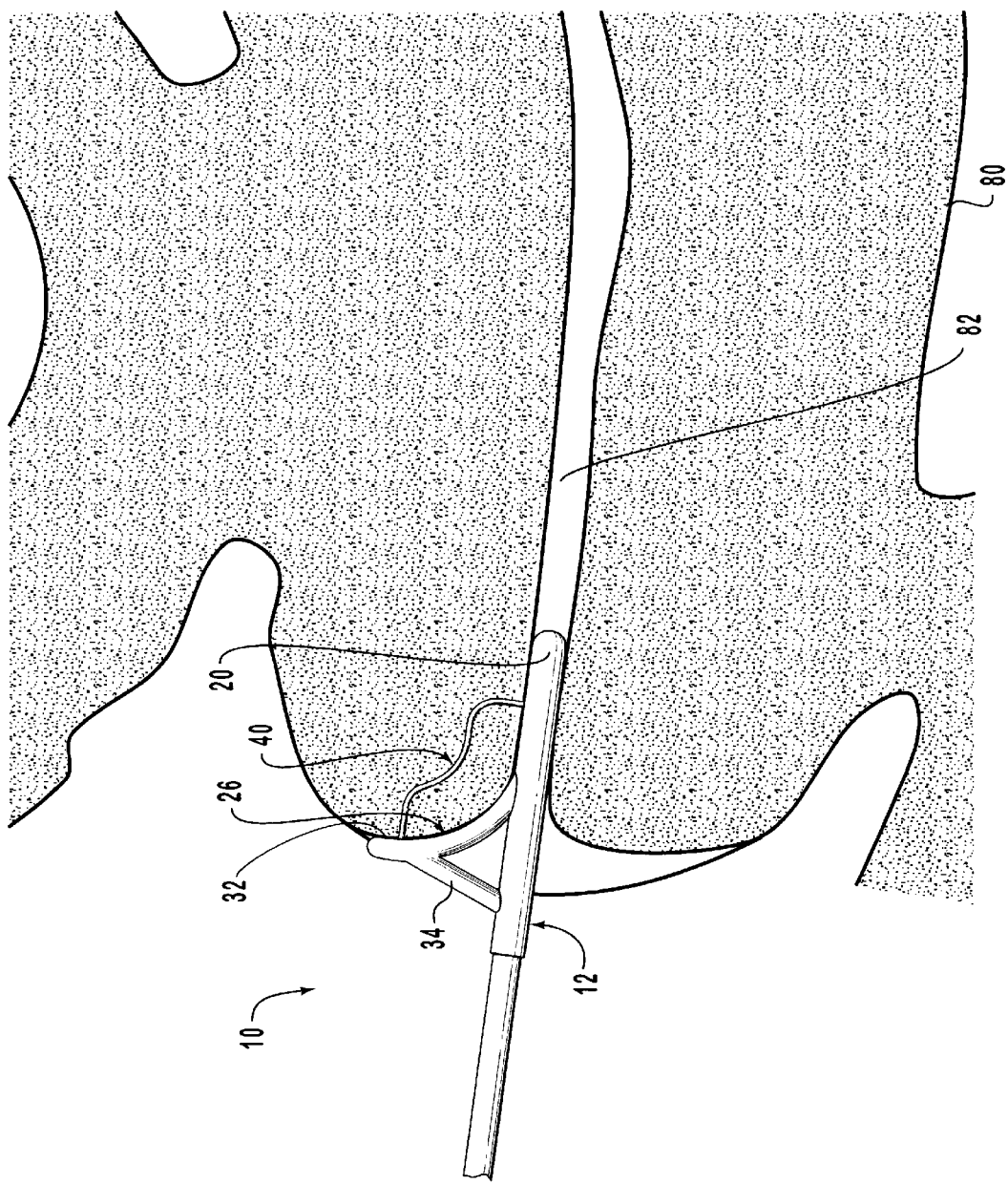
FIG. 3 is a cross-sectional side view of a uterus and uterine cervical canal illustrating the insertion of the operative tip and conducting member into the cervical canal for excision of a tissue sample by the instrument of the present invention.

One presently preferred embodiment of the present invention, designated generally at 10, is best illustrated in FIGS. 1 and 2. As shown, an endocervical conization electrode apparatus 10 includes a non-conductive support assembly 12 and a conducting member 40 having an anatomically-favorable curve adapted to limit excess removal of healthy tissue at the midsection and opposing ends of an excision site. The conducting member 40 is preferably composed of a material which is suitable to conduct high frequency electrical energy for cutting body tissue, such as, for example, a thin wire electrode. An electrosurgical generator 52 electrically communicates with the wire electrode 40 by means of an adaptable connector 50 thereby allowing the electrosurgical generator 52 to selectively transmit sufficient high frequency electrical energy to the conducting member 40 so as to enable the conducting member to excise a tissue specimen from the uterine cervical canal 82, as best illustrated in FIG. 3.

In one presently preferred embodiment of the present invention, the support assembly 12 comprises an elongated, substantially cylindrical body having a first end 14, a second opposing end 16 and an intermediate body portion 18 disposed between the first and second ends 14, 16. An operative tip 20 is preferably formed contiguous the first end 14 of the support assembly 12. In structural design, the operative tip 20 comprises an elongated, substantially cylindrical configuration having a dimensional size sufficient for being received within the cervical canal 82 of a female uterus 80. Similarly, the operative tip 20 is preferably formed having a dimensional length sufficient to act as a pivot point in relation to the cervical canal when inserted therein.

In one presently preferred embodiment, the operative tip 20 is formed as a unitary component of the support assembly 12. It will be readily appreciated, however, that the operative tip 20 may be connected at the first end 14 of the support assembly 12 as a separate member, if desired.

In addition to the operative tip 20, the support assembly 12 comprises an extension arm 26 configured having a general arcuate shape. The extension arm 26 may be disposed substantially outward from the axis of the intermediate body portion 18 of the support assembly 12. Preferably, the extension arm 26 comprises a surface facing 32 having a general arcuate or concave shape disposed between its proximal and distal end 28, 30. In one presently preferred embodiment of the present invention, the surface facing 32 of the extension arm 26 extends arcuately away in a radial direction from a point of substantial tangency in relation to the intermediate body portion 18 of the support assembly 12. In structural design, the extension arm 26 includes a proximal end 28 rigidly fixed along the exterior of the intermediate body portion 18. As best shown in FIGS. 1 and 2, the proximal end 28 of the extension arm 26 is preferably secured approximate the intermediate body portion 18 at a position between the second end 16 of the support assembly 12 and the operative tip 20.

In operation, the general arcuate configuration and the disposition of the surface facing 32 provides a structural stop for limiting the insertion depth of the operative tip 20 of the support assembly 12 within the cervical canal 82, as best shown in FIG. 3. The surface facing 32 of the extension arm 26 contiguous its distal end 30 may further comprise a dimensional length that is sufficient to provide a structural stop for restricting the support member 12 from spiraling downward as the conducting member 40 excises a tissue specimen from the cervical canal.

In one presently preferred embodiment of the present invention, the extension arm 26 may be formed having a dimensional length between approximately 17 mm and 21 mm, and preferably about 19 mm. As will be readily appreciated, however, various other dimensional lengths and curvatures of the extension arm 26 and its surface facing 32 are possible which are consistent with the spirit and scope of the present invention.

The extension arm 26 may be structurally supported by a support member 34 rigidly secured in relation to the intermediate body portion 18 of the support assembly 12. For example, the support member 34 may comprise a dimensional length sufficient for being disposed between a distal end 30 of the extension arm 26 and a portion of the intermediate body 18 proximate the second end 16 of the support assembly 12. In this configuration, the support member 34 provides a means for supporting the concave shape of the surface facing 32 of the extension arm 26 which functions as a structural stop in relation to the insertion depth of the operative tip 20 into the cervical canal 82.

It will be apparent that other support mechanisms may be constructed in accordance with the inventive principles set forth herein. For example, the support member 34 may not be provided for supporting the structural integrity of the extension arm 26, but rather the extension arm 26 may be formed having sufficient rigidity so as to function independently as a structural stop without additional support. It is intended, therefore, that the examples provided herein be viewed as exemplary of the principles of the present invention, and not as restrictive to a particular structure for implementing those principles.

Figure 4:
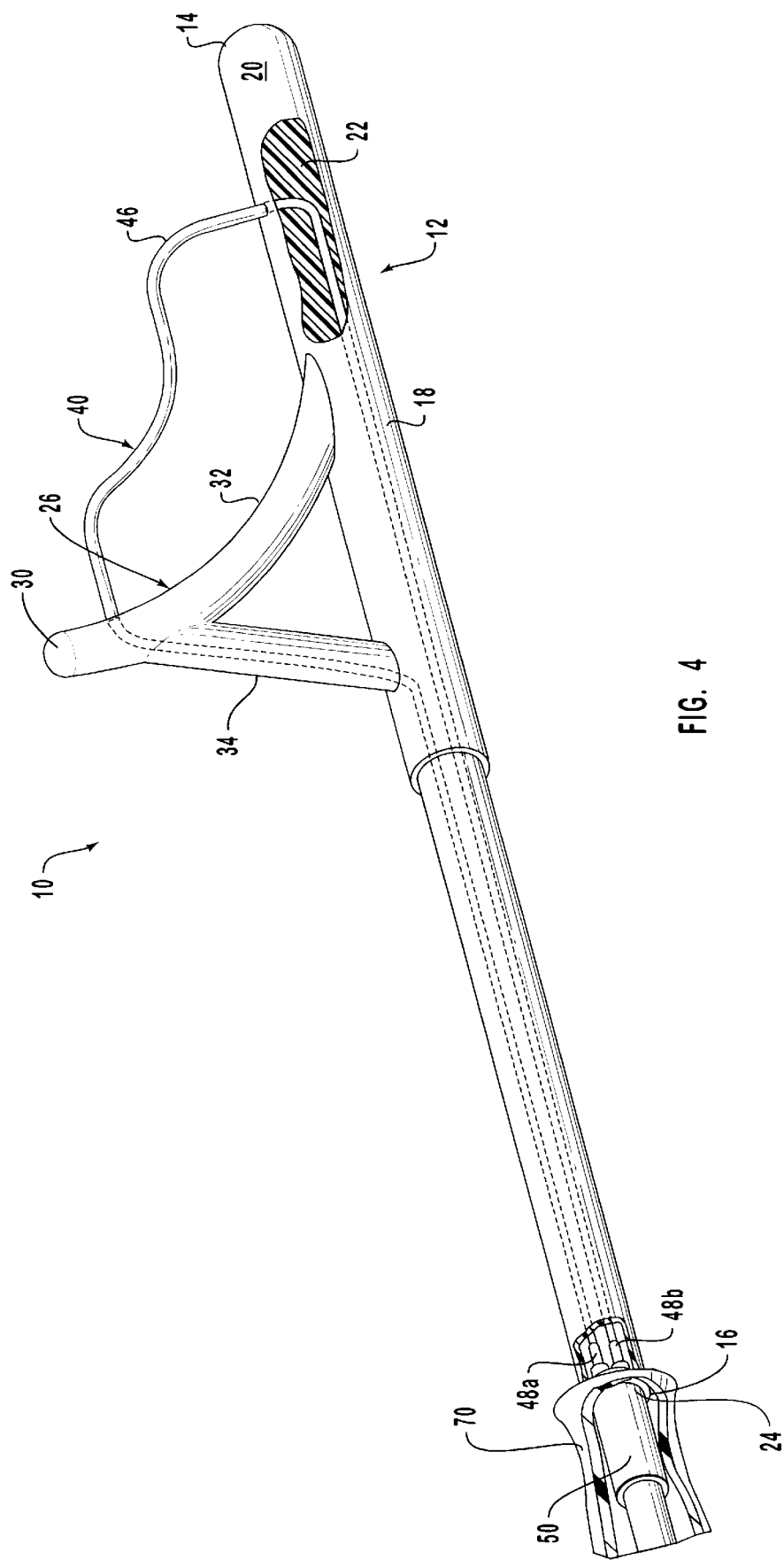
FIG. 4 is a cut-away sectional view of an embodiment of an endocervical conization electrode apparatus with a portion of the conducting member (shown in phantom lines) passing internally through the support assembly and engaging the adaptable connector.
Figure 5:
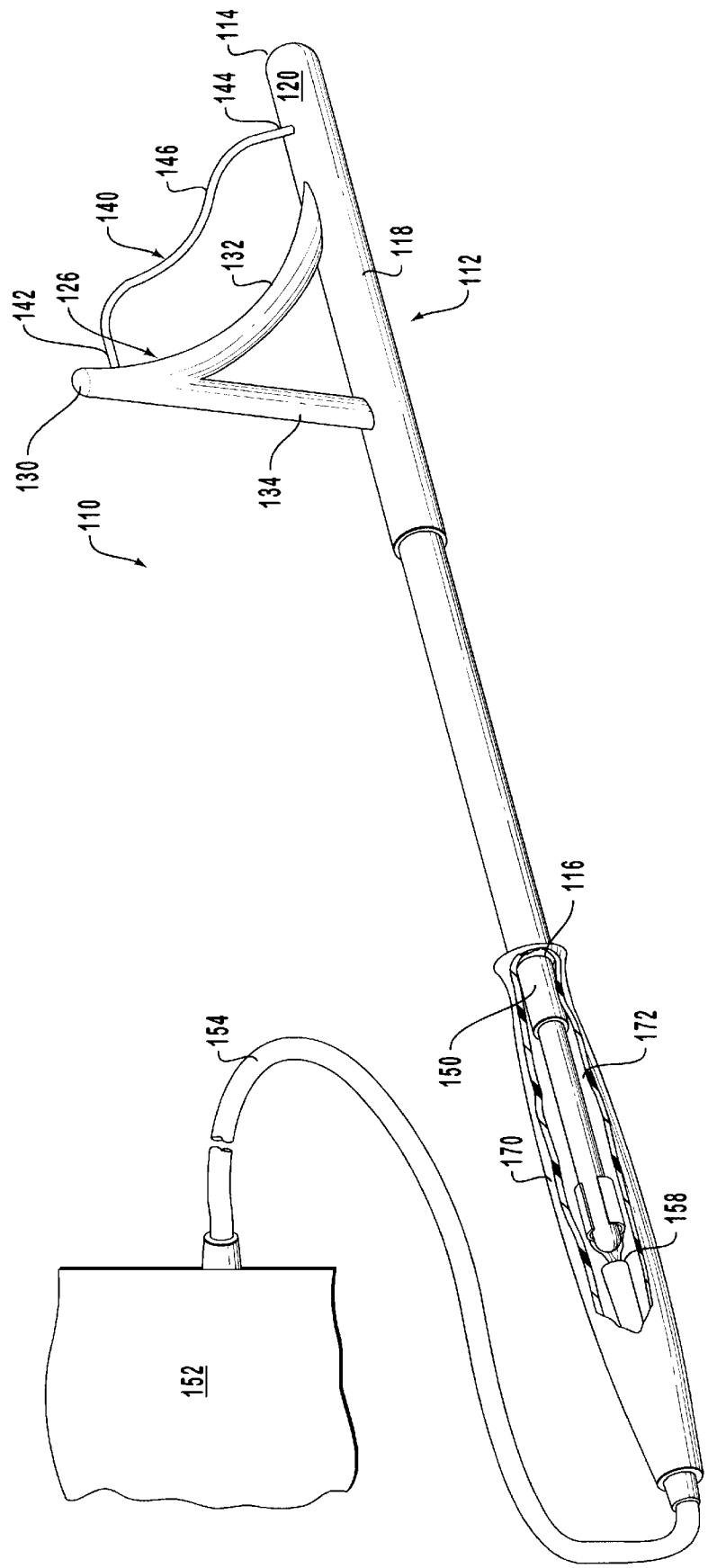
FIG. 5 is a perspective view of another presently preferred embodiment of the endocervical conization electrode apparatus illustrating a variation in the fixed placement of the extension member in relation to the intermediate body portion of the support assembly and, thereby, providing a diverse angular disposition of the surface facing of the extension member and including an angular variation in the curvilinear configuration of the conducting member.

Referring to FIG. 5, an alternate preferred embodiment of the endocervical conization electrode apparatus includes an extension arm 126 of the support assembly 112 comprising a surface facing 132 having a general arcuate configuration which defines a sharper angular facing in comparison to the embodiment illustrated in FIGS. 1 through 4. The surface facing 132 of the extension arm 126 contiguous its distal end 130 may comprises a dimensional length sufficient to provide a structural stop for restricting the support member 112 from spiraling downward as the conducting member 140 excises a tissue specimen from the cervical canal. It is intended, therefore, that the various embodiments provided herein be viewed as exemplary of the principles of the present invention, and not as restrictive to a particular structure for implementing those principles.

The support assembly 12, 112 is preferably comprised of a thermally stable material so that the support assembly will be unaffected by the heat produced by electrical energy passing through the conducting member 40, 140, as shown in FIGS. 1 and 5. For example, the material comprising the support assembly 12, 112 may be formed of any one of a variety of ceramic substrates commonly known and used in the art. As will be appreciated by those skilled in the art, the support assembly 12, 112 may be formed of polypropylene or of any other suitable composite or polymeric material having general mechanical and physical properties sufficient for withstanding elevated temperatures.

Consistent with the foregoing, the conducting member 40, 140 is preferably comprised of a material which is suitable to conduct high frequency electrical energy for cutting body tissue. In one presently preferred embodiment of the present invention, the conducting member 40, 140 comprises a wire electrode preferably formed of tungsten and generally configured as a conventional loop electrode. The conducting member 40, 140 may also be formed of stainless steel or any other compatible materials which are consistent with the spirit and scope of the present invention.

As best illustrated in FIGS. 1, 2 and 5, the conducting member 40, 140 comprises a contact portion 46, 146 extending between the extension arm 26, 126 and the first end 14, 114 of the support assembly 12, 112. In use, a surgeon can easily guide the operative tip 20, 120 into the cervical canal 82 and, respectively, introduce the contact portion 46, 146 of the conducting member 40, 140 into a position of desired contact with the cervical tissue of the uterus 80. As noted above, the concave configuration of the surface facing 32, 132 of the extension arm 26, 126 provides a structural stop limiting the insertion depth of the operative tip 20, 120 of the support assembly 12, 112 when inserted into the cervical canal 82, as illustrated in FIG. 3.

In structural design, the contact portion 46, 146 of the conducting member 40, 140 comprises an anatomically-favorable curve adapted to limit excess removal of healthy tissue at the midsection and opposing ends of an excision site. As shown, the anatomically-favorable curve formed in the body of the contact portion 46, 146 of the conducting member 40, 140 is preferably disposed between a first section 42, 142 extending substantially outward from the extension arm 26, 126 and a second section 44, 144 extending substantially outward from the intermediate body portion 18, 118 of the support assembly 12, 112. In particular, the contact portion 46, 146 of the conducting member 40, 140 may be formed having a general arcuate or concave configuration between the first section 42, 142 and the second section 44, 144.

Still referring to FIGS. 1, 2 and 5, the specific configuration of the anatomically-favorable curve of the contact portion 46, 146 in relation to the disposition of the extension arm 26, 126 provides a means for limiting excess removal of tissue at the midsection of an excision site and near the proximal end of the operative tip 20, 120. Consistent therewith, the contact portion 46, 146 of the conducting member 40, 140 is effective to be anatomically conformable to the surface of the cervical canal 82 so as to provide a tissue specimen having a substantially constant section upon circumferential rotation of the support assembly 12, 112 of the present invention 10, 110, as illustrated in FIG. 3.

Based on the nature and location of the diseased tissue, the configuration of the contact portion 46 of the conducting member 40, as illustrated in FIGS. 1 and 2, comprises an anatomically-favorable curve that facilitates a deeper cut in relation to the contact portion 146 of the conducting member 140, as illustrated in FIG. 5, which facilitates a narrower cut. In this regard, the tissue specimen excised from the cervical canal 82 may be formed having a general T-shaped or disc-shaped configuration.

Referring now to FIGS. 1 and 4, the first and second ends 48a, 48b of the conducting member 40 (e.g., wire loop electrode) may be housed within the support assembly 12. Specifically, formed within the intermediate body portion 18 of the support assembly 12 is an internal channel 22. The internal channel 22 preferably comprises an insulated core having an internal periphery sufficient for housing the first and second ends 48a, 48b of the conducting member 40 and at least a leading portion of an adaptable connector 50 electrically connected to the conducting member 40 by conventional means. Accordingly, an opening 24 is preferably formed at the second end 16 of the internal channel 22 of the support assembly 12. Functionally, the opening 24 at the second end 16 of the support assembly 12 provides a means for introducing at least a leading portion of the adaptable connector 50 into the internal channel 22. As those skilled in the art will appreciate, other embodiments in relation to the connecting portion of the first and second ends 48a, 48b of the conducting member 40 disposed within the internal channel 22 of the support assembly 12 may include conductive materials in the form of deposits, etchings, or sprays which are considered to be included within the spirit and scope of the present invention.

Referring now to FIGS. 1 and 5, a handle 70, 170 may be incorporated which comprises an interior cavity 72, 172 having an insulated periphery sufficient for receiving in mechanical engagement at least a portion of adaptable connector 50, 150 and accommodating the communication of electrical energy through a connecting wire 54, 154 which exits the proximal end of the handle 70, 170 and connects with an electrosurgical generator 52, 152. Preferably, the connecting wire 54, 154 is insulated and capable of carrying high frequency electrical energy to the conducting member 40, 140 through its distal end 58, 158 by means of an adaptable engagement with the adaptable connector 50, 150. In preferred design, the connecting wire 54, 154 exits the proximal end of the handle 70, 170 where it is enclosed within an insulated cable suitable for protecting the connecting wire.

In the presently preferred embodiments of the present invention, the electrosurgical generator 52, 152 is of a type commonly known and used in the industry for providing an adjustable output of high frequency electrical energy. By selectively controlling the output of the electrosurgical generator 52, 152, the operator or surgeon is able to transmit sufficient high frequency electrical energy to the conducting member 40, 140 to enable the conducting member to cut the desired body tissue when the endocervical conization electrode apparatus 10, 110 is properly positioned within the cervical canal 82 and thereby rotated about its axis.

Alternatively, the electrosurgical generator 52, 152 may electrically communicate with the conducting member 40, 140 directly, thereby eliminating the adaptable connector 50, 150. In such an embodiment, the electrosurgical generator 52, 152 delivers electrical energy to the conducting member 40, 140 through the connecting wire 54, 154 preferably enclosed within an insulated cable and disposed within the interior cavity 72, 172 of the handle 70, 170. Correspondingly, the connecting wire 54, 154 exits the proximal end of the handle 70, 170 and connects to an output of the electrosurgical generator 52, 152. As will be appreciated, those skilled in the art will recognize other possible modifications and adaptations which are consistent with the spirit and scope of the present invention. For instance, the connecting wire 54, 154 may enter from the midsection of the handle 70, 170 rather than from its proximal end.

Although the intermediate body portion 18, 118 and operative tip 20, 120 of the support assembly 12, 112 are illustrated and described in connection with having a general cylindrical shape, those skilled in the art will recognize that various other geometrical configurations are likewise suitable. The use of a generally cylindrical configuration is thus by way of illustration only and not by way of limitation.

As illustrated in FIG. 3, with the operative tip 20 inserted within the cervical canal 82 at a depth consistent with the structural stop as provided by the generally arcuate configuration of the surface facing 32 of the extension arm 26, the endocervical conization electrode apparatus 10 can be rotated about the longitudinal axis of the intermediate body portion 18 of the support assembly 12 thereby manipulating the conducting member 40 in a circular motion about the cervical canal 82 to excise a tissue sample for pathological study and diagnosis with operative precision and accuracy, while reducing unnecessary thermal exposure of healthy tissue at the midsection and opposing ends of the excision site that may result in reproductive and/or obstetric sequelae.

From the above discussion, it will be appreciated that the present invention provides novel electrosurgical cutting apparatus for excising a tissue specimen from a female uterine cervix by means of endocervical conization. In particular, the present invention provides a diagnostic and therapeutic modality designed to efficiently cut body tissue through the process of cell lysis using heat produced by electrical current concentrated at an endocervical site where cutting is desired.

Unlike prior art devices, the present invention provides an electrosurgical apparatus for performing endocervical conization comprising a wire electrode having an anatomically-favorable curve adapted to limit excess removal of tissue at the midsection and opposing ends of an excision site. Additionally, the present invention comprises a non-conductive support assembly having an operative tip sized for insertion through a uterine cervical canal and an extension member having peripheral edge configured in a general arcuate shape which facilitates a structural stop for limiting the insertion depth of the operative tip into the cervical canal. Consistent with the foregoing, the electrosurgical electrode apparatus of the present invention provides a means for performing endocervical conization with operative precision and accuracy, while providing a tissue specimen having a substantially constant section thereby reducing unnecessary thermal exposure of healthy tissue.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An electrosurgical cutting apparatus for excising a tissue specimen from a uterine cervix, said apparatus comprising:

a non-conductive support assembly including an operative tip having a size sufficient for insertion into a uterine cervical canal and an extension member comprising a surface facing configured having a general arcuate shape sufficient for facilitating a structural stop for limiting insertion of said operative tip into said cervical canal;

a conducting member extending between said extension member and said operative tip of said support assembly, said conducting member configured having an anatomically-favorable shape adapted to limit excess removal of healthy tissue at a midsection of an excision site; and an electrical connector for connecting said conducting member to an electrosurgical generator configured to selectively transmit high frequency electrical energy to the conducting member to enable the conducting member to excise said tissue specimen from said cervical canal.

2. An electrosurgical cutting apparatus as defined in claim 1 wherein said support assembly is composed of a thermally stable material.

3. An electrosurgical cutting apparatus as defined in claim 1 wherein said support assembly comprises an insulated core.

4. An electrosurgical cutting apparatus as defined in claim 1 wherein said operative tip comprises a dimensional length sufficient to act as a pivot point in relation to said cervical canal.

5. An electrosurgical cutting apparatus as defined in claim 1 wherein said extension member extends arcuately away in a radial direction from a point of substantial tangency in relation to said operative tip.

6. An electrosurgical cutting apparatus as defined in claim 1 wherein said support assembly further comprises a support member providing means for structurally supporting said extension member.

7. An electrosurgical cutting apparatus as defined in claim 1 wherein said anatomically-favorable shape of said conducting member comprises means for excising a tissue specimen having a substantially constant section.

8. An electrosurgical cutting apparatus as defined in claim 1 wherein said conducting member comprises a wire electrode.

9. An electrosurgical cutting apparatus as defined in claim 8 wherein said wire electrode comprises a tungsten wire.

10. An electrosurgical cutting apparatus as defined in claim 8 wherein said wire electrode comprises a stainless steel wire.

11. An electrosurgical cutting apparatus as defined in claim 1 wherein said conducting member forms a wire loop electrode.

12. An electrosurgical cutting apparatus as defined in claim 1 wherein said conducting member comprises an intermediate contact portion having a general concave configuration.

13. An electrosurgical cutting apparatus as defined in claim 1 wherein a portion of said conducting member is internal to said support assembly.

14. An electrosurgical cutting apparatus for excising a tissue specimen from a uterine cervix, said apparatus comprising:
   a non-conductive, thermally stable support assembly including an operative tip having a size sufficient for insertion into a uterine cervical canal and an extension member extending arcuately away in a radial direction from a point of substantial tangency in relation to said operative tip, said extension member facilitating a structural stop for limiting insertion of said operative tip into said cervical canal;
   a wire loop electrode operably extending between said extension member and said operative tip of said support assembly, said wire loop electrode being configured having an anatomically-favorable shape adapted to provide a tissue specimen having a substantially constant section upon excision and comprising an intermediate contact portion having a generally concave configuration; and
   an electrical connector for connecting said wire loop electrode to an electrosurgical generator configured to selectively transmit high frequency electrical energy to the wire loop electrode to enable the wire loop electrode to excise said tissue specimen from said cervical canal.

15. An electrosurgical cutting apparatus as defined in claim 14 further comprising a connecting wire adapted to extend between said electrical connector and said electrosurgical generator.

16. An electrosurgical cutting apparatus as defined in claim 14 further comprising a handle configured to receive in electrical and mechanical engagement said electrical connector.

17. An electrosurgical cutting apparatus as defined in claim 14 wherein said operative tip comprises a dimensional length sufficient to act as a pivot point in relation to said cervical canal.

18. An electrosurgical cutting apparatus as defined in claim 14 wherein said wire loop electrode comprises a tungsten wire.

19. An electrosurgical cutting apparatus as defined in claim 14 wherein said extension member comprises a dimensional length sufficient to restrict said support assembly from spiraling downward as said wire loop electrode excises said tissue specimen from said cervical canal.

20. An electrosurgical cutting apparatus as defined in claim 14 wherein a portion of said wire loop electrode is internal to said support assembly.

* * * * *